United States Patent
Kohlstruk et al.

(10) Patent No.: US 10,125,089 B2
(45) Date of Patent: Nov. 13, 2018

(54) PROCESS FOR PREPARING 3 AMINOMETHYL-3,5,5-TRIMETHYLCYCLOHEXYLAMINE

(71) Applicant: Evonik Degussa GmbH, Essen (DE)

(72) Inventors: Stephan Kohlstruk, Gladbeck (DE); Anne Rittsteiger, Olfen (DE); Alexander Martin Rüfer, Recklinghausen (DE); Norbert Schlüter, Gescher (DE); Sven Schneider, Datteln (DE); Sabrina Sowka, Dülmen (DE); Guido Streukens, Wuppertal (DE); Stefan Röder, Sinntal (DE); Monika Berweiler, Maintal (DE)

(73) Assignee: Evonik Degussa GmbH, Essen (DE)

( * ) Notice: Subject to any disclaimer, the term of this patent is extended or adjusted under 35 U.S.C. 154(b) by 1 day.

(21) Appl. No.: 15/541,733

(22) PCT Filed: Jan. 26, 2016

(86) PCT No.: PCT/EP2016/051503
§ 371 (c)(1),
(2) Date: Jul. 6, 2017

(87) PCT Pub. No.: WO2016/120235
PCT Pub. Date: Aug. 4, 2016

(65) Prior Publication Data
US 2017/0362163 A1 Dec. 21, 2017

(30) Foreign Application Priority Data

Jan. 30, 2015 (EP) .................................. 15153287

(51) Int. Cl.
| | | |
|---|---|---|
| C07C 209/52 | (2006.01) | |
| B01J 25/00 | (2006.01) | |
| B01J 35/02 | (2006.01) | |
| C07C 209/48 | (2006.01) | |
| B01J 25/02 | (2006.01) | |
| B01J 37/00 | (2006.01) | |

(52) U.S. Cl.
CPC .......... *C07C 209/52* (2013.01); *B01J 25/00* (2013.01); *B01J 25/02* (2013.01); *B01J 35/023* (2013.01); *B01J 35/026* (2013.01); *B01J 37/0018* (2013.01); *B01J 37/0063* (2013.01); *B01J 37/0081* (2013.01); *C07C 209/48* (2013.01); *B01J 2523/00* (2013.01); *C07C 2601/14* (2017.05)

(58) Field of Classification Search
CPC . B01J 25/00; B01J 25/02; B01J 35/023; B01J 35/026; B01J 37/0018; B01J 37/0063; B01J 37/0081; B01J 2523/00; C07C 209/48; C07C 209/52; C07C 2601/14
See application file for complete search history.

(56) References Cited

U.S. PATENT DOCUMENTS

| | | | | |
|---|---|---|---|---|
| 2,903,438 | A | * | 9/1959 | Stautzenberger ........ B01J 25/04 210/732 |
| 3,352,913 | A | | 11/1967 | Schmitt et al. |
| 4,429,157 | A | | 1/1984 | Disteldorf et al. |
| 5,371,292 | A | * | 12/1994 | Merger ................. C07C 209/26 558/430 |
| 5,491,264 | A | | 2/1996 | Herkes et al. |
| 5,504,254 | A | | 4/1996 | Haas et al. |
| 5,583,260 | A | | 12/1996 | Haas et al. |
| 5,679,860 | A | | 10/1997 | Haas et al. |
| 5,852,217 | A | | 12/1998 | Haas et al. |
| 6,011,179 | A | | 1/2000 | Haas et al. |
| 6,284,703 | B1 | | 9/2001 | Ostgard et al. |
| 6,337,300 | B1 | | 1/2002 | Sauer et al. |
| 6,489,521 | B2 | | 12/2002 | Ostgard et al. |
| 6,552,154 | B1 | | 4/2003 | Kohlstruk et al. |
| 6,573,213 | B1 | | 6/2003 | Ostgard et al. |
| 6,649,799 | B2 | | 11/2003 | Ostgard et al. |
| 6,730,628 | B2 | | 5/2004 | Kohlstruk et al. |
| 6,747,180 | B2 | | 6/2004 | Ostgard et al. |

(Continued)

FOREIGN PATENT DOCUMENTS

| | | |
|---|---|---|
| CN | 104230721 A | 12/2014 |
| DE | 4426472 A1 | 2/1995 |

(Continued)

OTHER PUBLICATIONS

German language International Search Report dated Apr. 12, 2016 in PCT/EP2016/051503 (5 pages).

(Continued)

*Primary Examiner* — Pancham Bakshi
*Assistant Examiner* — Mark R Luderer
(74) *Attorney, Agent, or Firm* — Nexsen Pruet, PLLC; Philip P. McCann

(57) ABSTRACT

Process for preparing isophoronediamine, characterized in that

A) isophoronenitrile is subjected directly in one stage to aminating hydrogenation to give isophoronediamine in the presence of ammonia, hydrogen, a hydrogenation catalyst and possibly further additions, and in the presence or absence of organic solvents;

or

B) isophoronenitrile is first converted fully or partly in at least two or more than two stages to isophoronenitrile imine, and this isophoronenitrile imine is subjected to aminating hydrogenation to give isophoronediamine as a pure substance or in a mixture with other components and/or isophoronenitrile, in the presence of at least ammonia, hydrogen and a catalyst.

27 Claims, 1 Drawing Sheet

(56) References Cited

U.S. PATENT DOCUMENTS

| | | |
|---|---|---|
| 6,794,331 B2 | 9/2004 | Ostgard et al. |
| 6,800,714 B2 | 10/2004 | Kohlstruk et al. |
| 7,632,967 B2 | 12/2009 | Ostgard et al. |
| 8,877,976 B2 | 11/2014 | Lettmann et al. |
| 9,035,102 B2 | 5/2015 | Nitz et al. |
| 9,085,506 B2 | 7/2015 | Galle et al. |
| 2001/0018402 A1 | 8/2001 | Ostgard et al. |
| 2002/0038051 A1 | 3/2002 | Ostgard et al. |
| 2002/0151436 A1 | 10/2002 | Ostgard et al. |
| 2003/0120116 A1 | 6/2003 | Ostgard et al. |
| 2003/0203812 A1 | 10/2003 | Ostgard et al. |
| 2004/0199007 A1 | 10/2004 | Ostgard et al. |
| 2004/0260120 A1 | 12/2004 | Ostgard et al. |
| 2010/0041921 A1* | 2/2010 | Lettmann .............. C07C 209/48 564/445 |
| 2016/0152496 A1 | 6/2016 | Kreczinski et al. |
| 2016/0272580 A1 | 9/2016 | Nitz et al. |
| 2016/0289164 A1 | 10/2016 | Kohlstruk et al. |
| 2017/0152217 A1 | 6/2017 | Nitz et al. |

FOREIGN PATENT DOCUMENTS

| | | |
|---|---|---|
| EP | 0042119 A2 | 12/1981 |
| EP | 0061137 A1 | 9/1982 |
| EP | 0394967 A1 | 10/1990 |
| EP | 0449089 A1 | 10/1991 |
| EP | 0816323 A2 | 1/1998 |
| EP | 913387 A2 | 5/1999 |
| EP | 2649042 A1 | 10/2013 |
| WO | 2005039764 A1 | 5/2005 |
| WO | 2007028411 A1 | 3/2007 |
| WO | 2008107226 A1 | 9/2008 |
| WO | 2012076315 A1 | 6/2012 |
| WO | 2012126869 A1 | 9/2012 |

OTHER PUBLICATIONS

German language Written Opinion dated Apr. 12, 2016 in PCT/EP2016/051503 (7 pages).
International Search Report dated Apr. 12, 2016 in PCT/EP2016/051503 (3 pages).
Langkabel et al., U.S. Appl. No. 15/602,723, filed May 23, 2017.
Langkabel et al., U.S. Appl. No. 15/603,966, filed May 24, 2017.
Langkabel et al., U.S. Appl. No. 15/604,118, filed May 24, 2017.
Rittsteiger et al., U.S. Appl. No. 15/473,892, filed Mar. 30, 2017.
Rittsteiger et al., U.S. Appl. No. 15/642,382, filed Jul. 6, 2017.
Rufer et al., U.S. Appl. No. 15/604,873, filed May 25, 2017.
Rufer et al., U.S. Appl. No. 15/604,988, filed May 25, 2017.
Rufer et al., U.S. Appl. No. 15/605,268, filed May 25, 2017.

* cited by examiner

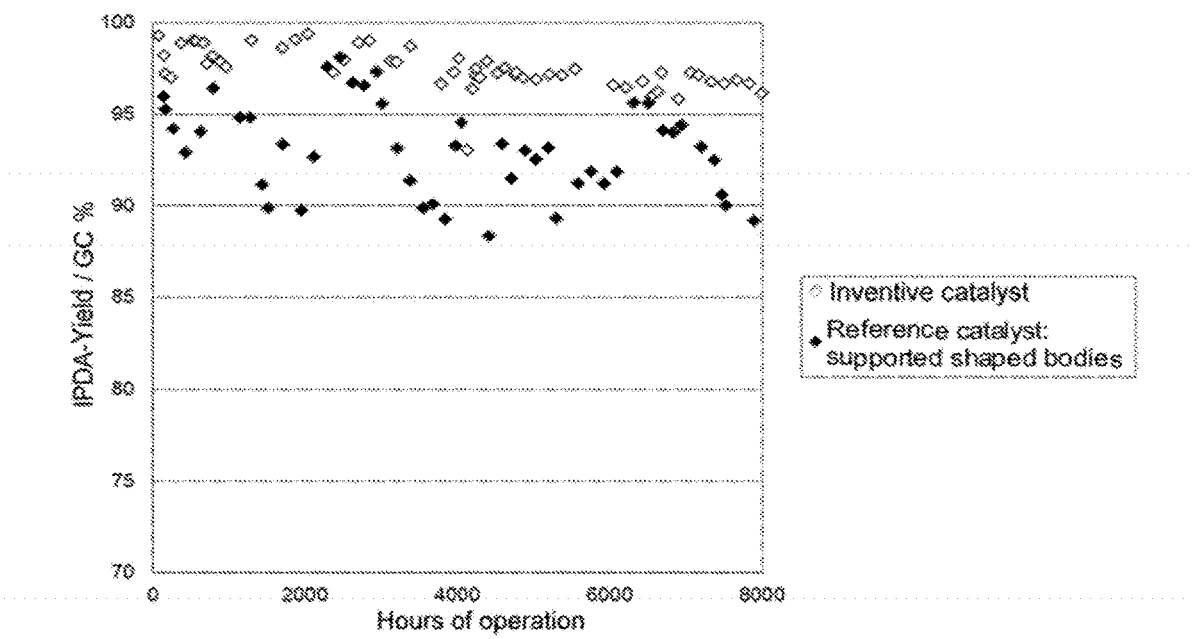

PROCESS FOR PREPARING 3 AMINOMETHYL-3,5,5-TRIMETHYLCYCLOHEXYLAMINE

This application is a national stage application under 35 U.S.C. § 371 of International Application No. PCT/EP2016/051503 filed 26 Jan. 2016, which claims priority to EP Application No. 15153287.6 filed 30 Jan. 2015, the disclosures of which are expressly incorporated herein by reference.

FIELD

The invention relates to an improved process for preparing 3-aminomethyl-3,5,5-trimethylcyclohexylamine, called isophoronediamine or IPDA for short hereinafter, by means of catalytic hydrogenation and/or catalytic reductive amination (also referred to as aminating hydrogenation) of 3-cyano-3,5,5-trimethylcyclohexanone, called isophoronenitrile or IPN for short hereinafter.

BACKGROUND

The preparation of IPDA by aminating hydrogenation of IPN is known and has already been described many times.

In the simplest case (U.S. Pat. No. 3,352,913), IPN is reacted in the presence of hydrogen and of an excess of ammonia over a cobalt catalyst. First of all, IPN and ammonia eliminate water to form isophoronenitrile imine, IPNI, which is subsequently hydrogenated to IPDA.

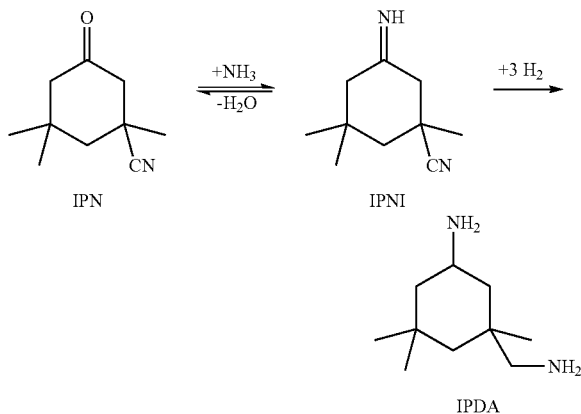

When the reaction is conducted in this way, the yield of IPDA is determined to a crucial degree by the excess of ammonia. The maximum IPDA yields achieved are about 80%. The main by-product is what is called the amino alcohol, IPAA, which results from the direct hydrogenation of the IPN.

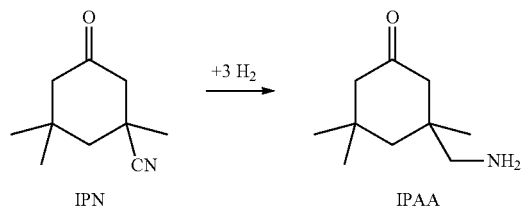

A significant rise in the IPDA yield is achieved when the formation of IPNI is accelerated by use of suitable imination catalysts. Suitable imination catalysts are, for example, acidic ion exchange resins (EP 042 119). In addition, it is also possible to use acidic metal oxides (EP 449 089), sulpho-containing organopolysiloxanes (EP 816 323), heteropolyacids (DE 44 26 472) and activated carbon (EP 061 137) as imination catalysts. As well as the reduction of the unwanted amino alcohol, other by-products are also distinctly suppressed, for example bicyclic compounds and those by-products which result from the elimination of HCN.

Particular reference is made to the problem of elimination of HCN from gamma-keto nitriles, such as IPN, in the literature (U.S. Pat. No. 3,352,913). Firstly, it is noted that HCN elimination reduces the yield of IPDA (EP 042 119, DE 44 26 472).

Secondly, it is pointed out that HCN acts as a catalyst poison and leads to deactivation of the hydrogenation catalyst (EP 394 967 A1, page 2 line 34 ff, page 3 line 44 ff). It is therefore advisable to conduct the imination step in such a way that a minimum amount of HCN is eliminated.

According to EP 913 387, selectivity can also be enhanced in the preparation of IPDA by using quaternary ammonium bases. Correspondingly modified catalysts, specifically in the case of use of a solvent, have a much longer service life than alkali-modified catalysts.

In addition, processes for preparing isophoronediamine are known from CN 104230721A, EP 2649042A and WO 2012126869A.

The underlying object was to find a process for preparing 3-aminomethyl-3,5,5-trimethylcyclohexylamine by hydrogenation of isophoronenitrile, wherein the yield and selectivity in the reductive amination of isophoronenitrile for preparation of isophoronediamine were to be improved.

SUMMARY

Surprisingly, a novel catalyst as described in detail below has been found. Additional unexpected effects found were a higher activity, which enables lower reaction temperatures, and a better long-term stability of the catalyst.

Typically, in processes for preparing 3-aminomethyl-3,5,5-trimethylcyclohexylamine by hydrogenation of isophoronenitrile, catalysts are used in the form of powders or shaped bodies, for example extrudates or compressed powders. It is possible to employ unsupported catalysts, Raney-type catalysts or supported catalysts. Preference is given to Raney-type and supported catalysts, as described in detail in EP 2649042A.

It has now been found that, surprisingly, the inventive catalyst consisting of a metal alloy in granular form of particular particle sizes, after activation by alkalis, achieves the object of the invention, and a higher activity and better long-term stability of the catalyst have additionally been found.

DETAILED DESCRIPTION

The invention provides a process for preparing isophoronediamine, characterized in that A) isophoronenitrile is subjected directly in one stage to aminating hydrogenation to give isophoronediamine in the presence of ammonia, hydrogen, a hydrogenation catalyst and possibly further additions, and in the presence or absence of organic solvents;

or

B) isophoronenitrile is first converted fully or partly in at least two or more than two stages to isophoronenitrile imine, and this isophoronenitrile imine is subjected to aminating hydrogenation to give isophoronediamine as a pure substance or in a mixture with other components and/or isophoronenitrile, in the presence of at least ammonia, hydrogen and a catalyst;

where the catalyst has the following properties:

I.

The catalyst has, after the activation, in its entirety, the following composition in percent by weight (% by weight), where the proportions add up to 100% by weight, based on the metals present:

cobalt: 55% to 95% by weight
aluminium: 5% to 45% by weight
chromium: 0% to 3% by weight
nickel: 0% to 7% by weight
and

II.

The catalyst is in the form of irregular particles as a granular material and, after the activation, has particle sizes of 1 to 8 millimeters (mm).

Catalyst

The catalyst consists of a metal alloy, the metal alloy having been surface activated by bases. The layer thickness of the activated layer on the particle surface of the catalyst is preferably 50 to 1000 micrometers (μm). It may also be greater or smaller. Accordingly, the catalytically active composition of the catalyst is present on the surface. Alternatively, it is possible in the context of the invention to almost entirely or entirely leach out the entire catalyst particle.

The inventive catalyst, after the activation, is present as granules in the form of individual particles.

After the activation, the inventive catalyst has, in its entirety, the following composition in percent by weight (% by weight), where the proportions add up to 100% by weight, based on the metals present:

1st Variant
cobalt: 55% to 95% by weight
aluminium: 5% to 45% by weight
chromium: 0% to 3% by weight
nickel: 0% to 7% by weight
or
2nd Variant
cobalt: 55% to 90% by weight
aluminium: 5% to 44.5% by weight
chromium: 0.5% to 5% by weight
or
3rd Variant
cobalt: 55% to 88% by weight
aluminium: 5% to 44.5% by weight
nickel: 0.5% to 7% by weight
or
4th Variant
cobalt: 55% to 85% by weight
aluminium: 5% to 43.5% by weight
chromium: 0.5% to 3% by weight
nickel: 1% to 7% by weight
5th Variant
cobalt: 57% to 84% by weight
aluminium: 10% to 40% by weight
chromium: 1% to 2% by weight
nickel: 2% to 4% by weight "Entirety" means that there is no distinction in the composition between the content of the metals on the surface and in the activated layer and in the core of the catalyst particles; instead, everything is added together and calculated.

The catalyst is in the form of irregular particles, i.e. of granules.

In addition, the inventive catalyst, after the activation, has the following particle sizes:

In general, the catalyst, i.e. the granule particles, may have particle sizes of 1 to 8 millimeters (mm).

In a first preferred variant of the invention, the particle sizes of the catalyst, i.e. the granule particles, vary from 2.5 to 6 millimeters (mm).

In a second preferred variant of the invention, the particle sizes of the catalyst, i.e. the granule particles, vary from 3 to 7 millimeters (mm).

In a third preferred variant of the invention, the particle sizes of the catalyst, i.e. the granule particles, vary from 2 to 5 millimeters (mm).

The particle sizes reported may also have a statistical distribution of size within the ranges. In this context, narrow distributions and also broad distributions are in accordance with the invention.

The determination of the particle sizes is described in DIN ISO 9276-1 (September 2004) and 9276-2 (February 2006) and 9276-4 (February 2006) and 9276-6 (January 2012). In addition, exact details of the definition of particle sizes, the distribution of particle sizes and the measurement of particle sizes can be found in HORIBA® Scientific, A GUIDEBOOK TO PARTICLE SIZE ANALYSIS, 2012, from HORIBA® Instruments, Inc, Irvine, USA.

According to the invention, the distribution of the particle sizes and the measurement of the particle sizes can be determined by laser methods (ISO 13320, 2012), light methods or imaging methods.

Preferably, the inventive catalyst is obtained by screening the granules produced. This produces what are called screen fractions. This may involve mixing individual screen fractions, or a catalyst is obtained by single or multiple screening. The catalysts thus produced have a statistical distribution for the particle sizes, typically in the form of a Gaussian distribution. Symmetric and also asymmetric distributions are possible.

In a fourth preferred variant of the invention, the particle sizes of the catalyst, i.e. the granule particles, vary with a statistical distribution between 2.5 and 5.5 millimeters (mm), where up to 10 percent of the particles may also be outside said range of said lower limit or upper limit, but up to 10 percent in each case may also be outside said range of said lower limit and upper limit.

In a fifth preferred variant of the invention, the particle sizes of the catalyst, i.e. the granule particles, vary with a statistical distribution between 3.5 and 6.5 millimeters (mm), where up to 10 percent of the particles may also be outside said range of said lower limit or upper limit, but up to 10 percent in each case may also be outside said range of said lower limit and upper limit.

In a sixth preferred variant of the invention, the particle sizes of the catalyst, i.e. the granule particles, vary with a statistical distribution between 2 and 5 millimeters (mm), where up to 10 percent of the particles may also be outside said range of said lower limit or upper limit, but up to 10 percent in each case may also be outside said range of said lower limit and upper limit.

In a seventh preferred variant of the invention, the particle sizes of the catalyst, i.e. the granule particles, vary with a statistical distribution between 3 and 7 millimeters (mm), where up to 10 percent of the particles may also be outside said range of said lower limit or upper limit, but up to 10 percent in each case may also be outside said range of said lower limit and upper limit.

Suitable methods and descriptions of screen analysis are given in:

DIN 66165-1:1987-04 Particle size analysis; sieve analysis; general principles, and in DIN 66165-2:1987-04 Particle size analysis; sieve analysis; procedure.

Paul Schmidt, Rolf Körber, Matthias Coppers: *Sieben and Siebmaschinen: Grundlagen and Anwendung* [Screens and Screening Machines: Fundamentals and Application], Wiley-VCH Verlag, 2003, ISBN 9783527302079, Chapter 4.4: Analysesiebung [Analytical Screening]. Törg Hoffmann: *Handbuch der Messtechnik* [Handbook of Measurement Technology], Hanser Verlag, 2007, ISBN 978-3-446-40750-3, Chapter 3.12.16.2.1.

After the activation, the inventive catalyst more preferably has, in its entirety, the following composition in percent by weight (% by weight), where the proportions add up to 100% by weight, based on the metals present:

cobalt: 57% to 84% by weight
aluminium: 10% to 40% by weight
chromium: 1% to 2% by weight
nickel: 2% to 4% by weight
and with particle sizes of the catalyst, i.e. the granule particles, having a statistical distribution between 2.5 and 5.5 millimeters (mm), or particle sizes of the catalyst, i.e. the granule particles, having a statistical distribution between 3.5 and 6.5 millimeters (mm), or particle sizes of the catalyst, i.e. the granule particles, having a statistical distribution between 2 and 5 millimeters (mm), or particle sizes of the catalyst, i.e. the granule particles, having a statistical distribution between 3 and 7 millimeters (mm), where up to 10 percent of the particles may also be outside said range of said lower limit or upper limit, but up to 10 percent in each case may also be outside said range of said lower limit and upper limit.

General Method for Production of the Catalyst:

a) Production of the Alloy

The alloy is produced by thermal means, for example in an induction oven. This involves melting the metals to obtain an alloy. The finished melt is cast to bars, for example, for further processing.

b) Production of the Granules

The alloy is processed to granules in suitable equipment, for example precomminuted by means of a jaw crusher and ground further by means of a roll mill. A screening step gives the desired size distribution of the granules through the choice of the appropriate screens (e.g. 3-7 mm).

c) Activation of the Catalyst

The catalyst is activated in suitable apparatus. It is possible here to use organic or inorganic bases. Preference is given to using an alkali (e.g. sodium hydroxide solution), in which case an exothermic operation results in leaching of a portion of the aluminium out of the alloy with formation of hydrogen and alkali metal aluminate. The concentration of the alkali may be between 5% and 30% by weight, and the reaction temperature between 50 and 100° C. The degree of activation is determined via the temperature and the reaction time. The reaction time is variable and depends on the reaction conditions and the desired degree of activation. After the activation, the catalyst is washed with water and then stored under water.

Other compositions can be produced analogously in the production step a) through the appropriate choice of the amounts of metals.

Preferably, the catalyst is produced in the sequence described. Alternatively, the catalyst can be activated prior to the production of the granules.

To increase the activity, selectivity and/or service life, the catalysts may additionally comprise doping metals or other modifiers. Typical doping metals are, for example, Mo, Fe, Ag, V, Ga, In, Bi, Ti, Zr and Mn, and the rare earths, alone or in mixtures. Typical modifiers are, for example, those with which the acid-base properties of the catalysts can be influenced, preferably alkali metals and alkaline earth metals or compounds thereof, preferably magnesium and lithium compounds. If compounds of this kind are present, in an amount of not more than about 5% by weight, there is correspondingly a reduction in the proportion of the above-mentioned Co and Al and any Cr and Ni metals in the catalyst, in which case the proportions of Co and Al and any Cr and Ni after the activation add up to at least 95% by weight, based on the metals present.

It is possible to conduct the process according to the invention in one stage or in at least two or more than two stages.

If the process is conducted in one stage, isophoronenitrile is subjected to aminating hydrogenation directly in the presence of ammonia, hydrogen, a catalyst and possibly further additions, and in the presence or absence of organic solvents.

The expression "in at least two or in more than two stages" means that isophoronenitrile is first converted fully or partly in a separate reactor or reactor section to isophoronenitrile imine, and this isophoronenitrile imine is subjected to aminating hydrogenation as a pure substance or in a mixture with other components, for example unconverted isophoronenitrile, in the presence of at least ammonia and hydrogen and a catalyst.

A preferred embodiment of the process according to the invention for preparing IPDA is a two-stage process: In the first stage, at least some of the IPN used, in the presence or absence of an imination catalyst and/or of solvents, is converted by reaction with ammonia to isophoronenitrile imine. The conversion of IPN to IPNI after the imination should be greater than 80%, preferably greater than 90%, more preferably greater than 95%.

In the second stage, the first stage reaction product, as obtained or after a further treatment and/or addition of further ammonia, is subjected to aminating hydrogenation over hydrogenation catalysts in the presence of at least ammonia and hydrogen and in the presence or absence of an organic solvent at a temperature of 20 to 150° C., preferably 40 to 130° C., and a pressure of 0.3 to 50 MPa, preferably 5 to 30 MPa.

In a further preferred embodiment, the conversion of IPN to IPDA is effected in three separate reaction spaces. In the first reaction space, IPN is converted to isophoronenitrile imine with excess ammonia over imination catalysts at temperatures between 20 and 150° C. and pressures between 5 and 30 MPa. In the second reaction space, the reaction products formed are hydrogenated with hydrogen in the presence of excess ammonia over hydrogenation catalysts at temperatures between 20 and 130° C. and pressures of 5 to 30 MPa. In the third reaction space, the reaction products formed are hydrogenated over the catalysts for use in accordance with the invention at temperatures between 100 and 160° C. and pressures of 5 to 30 MPa.

In order to accelerate the establishment of equilibrium in the imination reaction, it is appropriate to use an imination catalyst. For this purpose, the imination catalysts known according to the prior art can be used. Suitable catalysts are, for example, inorganic or organic ion exchangers (see EP 042 119), supported heteropolyacids (see DE 44 26 472), acidic metal oxides, especially aluminium oxide and titanium dioxide (see EP 449 089), organopolysiloxanes containing sulpho groups (DE 196 27 265.3), and acidic zeolites and activated carbon (EP 061 137). In the case of use of an imination catalyst, the reaction temperature may be between 10 and 150° C., preferably between 30 and 130° C. and most preferably between 40 and 100° C. The pressure is between the autogenous pressure of the mixture and 50 MPa. Preference is given to conducting the imination reaction at the pressure at which the subsequent reductive amination is also conducted.

Even though the imination of isophoronenitrile with liquid ammonia is preferably conducted without addition of further solvents, it is also possible to work in the presence of additional solvents. Suitable solvents are monohydric alcohols having 1 to 4 carbon atoms, especially methanol, and ethers, particularly THF, MTBE and dioxane.

In the imination stage, between 1 and 500 mol, preferably 5 and 200 mol, more preferably between 5 and 100 mol, of ammonia are used per mole of IPN used. Typical catalyst hourly space velocities are in the range from 0.01 to 10 kg of IPN per kg of catalyst and hour, preferably 0.5 to 10 and more preferably 0.5 to 5 kg of IPN per kg of catalyst and hour.

In the case of imination in the presence of an imination catalyst, the catalyst may be present in the form of a suspension catalyst or fixed bed catalyst. It is advantageous to use fixed bed catalysts. In a particularly preferred embodiment, IPN and ammonia are passed continuously from the bottom upward through a reaction tube filled with imination catalyst.

The hydrogenation is effected in fixed bed reactors. Suitable reactor types are, for example, shaft furnaces, tray reactors or shell and tube reactors.

The hydrogenation is typically effected at temperatures between 20 and 150° C., preferably 40 and 130° C., and pressures of 0.3 to 50 MPa, preferably 5 to 30 MPa. It is also possible to perform the hydrogenation in the presence of the solvents already mentioned for the imination stage. The main advantage in the case of use of a solvent is that the hydrogenation can be conducted at lower pressures between 0.3 and 10 MPa.

The hydrogen required for the hydrogenation can be supplied to the reactor either in excess, for example at up to 10 000 molar equivalents, or only in such an amount that the hydrogen consumed by reaction and the portion of the hydrogen which leaves the reactor dissolved in the product stream is replenished. In the case of a continuous mode of operation, the hydrogen can be supplied in cocurrent or countercurrent.

In a preferred embodiment, the hydrogenation is effected in liquid ammonia as solvent. Between 1 and 500 mol, preferably 5 and 200 mol, more preferably between 5 and 100 mol, of ammonia are used per mole of IPN. It is appropriate to use at least the amount of ammonia which has been established in the upstream imination. However, the ammonia content can also be increased to the desired value before the hydrogenation by addition of additional ammonia.

The required volume of the hydrogenation catalysts to be used is guided by the LHSV (liquid hourly space velocity), which is dependent on the operating pressure, the temperature, the concentration and the catalyst activity and has to be observed in order to ensure maximum completeness of hydrogenation of the IPN used. Typically, the LHSV in the case of use of the mixture of IPN, ammonia and hydrogen, the use of which is preferred, is between 0.5 and 5 liters of IPN/ammonia mixture per liter of catalyst and hour, preferably between 1 and 4 $l_{sol} l_{cat}^{-1} h^{-1}$.

It is preferable that the hydrogenation catalysts for use are first conditioned with ammonia before they are used in the hydrogenation. For this purpose, the catalysts are contacted with ammonia or with mixtures of ammonia and one or more solvents. The conditioning preferably follows installation of the catalysts in the hydrogenation reactor, but it can also precede the installation of the catalysts. For conditioning, between 0.2 and 3, preferably 0.5 and 2, m³ of ammonia per m³ of catalyst and hour are used. It is customary to work at temperatures between 20 and 150° C., preferably 40 to 130° C. Particular preference is given to running through a temperature ramp in which the catalyst, beginning at moderately elevated temperature, preferably between 20 and 50° C., is heated gradually up to the reaction temperature desired at a later stage for the hydrogenation, preferably 20 to 150° C. The conditioning is preferably conducted in the presence of hydrogen, the partial pressure of the hydrogen used in the reactor covering the range from 0.1 to 50 MPa, preferably 5 to 40 MPa, more preferably 10 to 30 MPa. The duration of the conditioning, depending on the amount of ammonia used, is preferably between 1 and 48 h, more preferably between 12 and 24 h.

In the preferred two-stage process, the mixture comprising isophoronenitrile imine is hydrogenated in the presence of the hydrogenation catalyst in the second stage. The mixture supplied to the hydrogenation stage may directly be any which is obtained in the imination of IPN with ammonia in the first stage, or as obtained after addition or removal of components, for example ammonia, organic solvents, bases, cyanide salts, hydrocyanic acid and/or water. Preference is given to conducting the hydrogenation continuously in fixed bed reactors which can be operated in trickle mode or liquid phase mode. Suitable reactor types are, for example, shaft furnaces, tray reactors or shell and tube reactors. It is also possible to connect a plurality of fixed bed reactors in series for the hydrogenation, in which case each of the reactors is operated either in trickle bed mode or liquid phase mode.

Apart from the aforementioned constituents of the mixture to be supplied to the imination stage, this may additionally comprise higher- or lower-boiling fractions than IPDA from the distillative workup of the reaction mixture drawn off from the trickle bed reactor. Such fractions may, apart from residues of IPDA, also comprise those by-products from which IPDA forms again under reaction conditions. It is particularly advantageous to recycle the higher-boiling fraction than IPDA, which, apart from residues of IPDA, comprises 2-aza-4,6,6-trimethylbicyclo [3.2.1]octane as the main product. It is likewise particularly advantageous to recycle incompletely converted IPN, especially fractions comprising isophoroneaminonitrile. The recycled material can also, if desired, be added directly to the reaction mixture to be supplied to the hydrogenation stage.

In the hydrogenation of IPN or isophoronenitrile imine, it is possible to form two different stereoisomers. Through the choice of a temperature profile in the hydrogenation step, it is possible to influence the isomer ratio. It is possible, for example, first to partly hydrogenate a mixture comprising IPN or isophoronenitrile imine at a temperature between 20 and 90° C., and then to complete the reaction in a second step within a temperature range between 90 and 150° C. Through the observation of relatively low reaction temperatures in the 1st step, the selectivity can be shifted in favour of the cis isomer. The observation of relatively low reaction temperatures at the start of the reaction additionally has the advantage that the thermally labile isophoronenitrile imine is hydrogenated under particularly gentle conditions, and side reactions are suppressed as a result. Isophoroneaminonitrile, which is formed as an intermediate, is much more thermally stable and can therefore be hydrogenated at higher temperatures without any risk of further side reactions. The unwanted side reactions also include the elimination of HCN. In the process according to the invention, a certain cyanide ion concentration has a positive effect on the selectivity of the hydrogenation stage. This effect becomes increasingly apparent when the cyanide ions are present from the start in the hydrogenation stage and not just formed during the hydrogenation. Therefore, elimination of HCN during the hydrogenation stage should be avoided.

The desired temperature profile can be implemented, for example, by the series connection of two or more separately heatable reactors. It is also possible to implement a rising temperature profile in only one hydrogenation reactor. Particular preference is given to conducting the hydrogenation reaction in an adiabatically operated trickle bed reactor, in which the reaction mixture is supplied to the reactor at temperatures between 20 and 90° C., and owing to the heat of reaction which occurs and is absorbed by the reaction mixture leaves it again between 90 and 150° C.

The reaction mixture leaving the hydrogenation is purified further by the customary methods, in order to obtain an IPDA with the desired quality. It is possible here to use all standard separation methods, for example distillation, flash evaporation, crystallization, extraction, sorption, permeation, phase separation or combinations of the above. The purification can be conducted continuously, batchwise, in one or more stages, under reduced pressure or under pressure. Possible components which are removed, for example, in the further purification are hydrogen, ammonia, water, and by-products obtained in the preparation of IPDA from IPN, for example hydrogenated HCN elimination products or impurities in the IPN, methylated by-products and/or incompletely hydrogenated intermediates.

Preferably, the purification is achieved by distillation under pressure and/or under reduced pressure in a plurality of steps. For this purpose, it is possible to use any desired distillation columns with or without internals, for example dephlegmators, dividing walls, unordered internals or random packings, ordered internals or structured packings, or trays with or without forced flow.

In a first step, especially hydrogen, inert gases, ammonia, low-boiling impurities and possibly also water are removed fully or partly in one or more distillation columns. The removal is preferably effected at a pressure lower than in the reaction step. If the removal is effected in a plurality of distillation steps, it is advantageous to lower the pressure stepwise. Most preferably, the removal is effected above 1 bar and with bottom temperatures of 0-200° C. The use of a stripping gas for removal of low-boiling impurities may be advantageous. Especially ammonia and hydrogen and proportions of the low-boiling impurities can be recycled fully or partly into the process (reaction). The low-boiling impurities and possibly proportions of hydrogen and ammonia are sent to thermal utilization.

In a second step, further low-boiling impurities, water and high-boiling impurities are fully or partly removed. This can be effected in one or more distillation columns. This may involve distilling water off together with organic, low-boiling impurities and possibly proportions of IPDA via the top of the column and, after condensation, separating them into an aqueous phase and an organic phase. In this case, the organic phase can be recycled partly as reflux into the column. If the second step of the distillation is conducted in a single column (for example a dividing wall column), the IPDA is withdrawn via a sidestream with the desired purity, while the high-boiling impurities are obtained in the bottom of the column. If the separation, however, is conducted in two or more stages, the IPDA is obtained at the top of a column. The low- and high-boiling impurities and water are preferably removed under a reduced pressure between 100 Pa and 0.0999 MPa and bottom temperatures of 50-300° C. All secondary components can be sent to thermal utilization.

Example

Production of the Catalyst, Cobalt Granules:
a) Production of the Alloy
The alloy is produced in an induction oven. This involves melting the metals in the appropriate amounts at 1500° C. The finished melt is cast to bars for further processing.
b) Production of the Granules
The alloy bars are precomminuted by means of a jaw crusher and ground further by means of a roll mill. A screening step gives the desired size distribution of the granules through the choice of the appropriate screens.
c) Activation of the Catalyst
The catalyst is activated in a standard glass laboratory apparatus, for example a beaker. An aqueous alkali (e.g. sodium hydroxide solution) was added to the granules while stirring. The granules are in a catalyst basket during the activation. An exothermic operation leaches a portion of the aluminium out of the alloy with formation of hydrogen and sodium aluminate solution. The concentration of the alkali used was 20% by weight and the reaction temperature was 90° C. The degree of activation was determined by the reaction time. After the activation, the catalyst is washed with water and then stored under water.

The catalyst used has, after the activation, in its entirety, the following composition in percent by weight (% by weight), where the proportions add up to 100% by weight, based on the metals present:
cobalt: 75.9% by weight
aluminium: 20.0% by weight
chromium: 1.5% by weight
nickel: 2.6% by weight A screen fraction was used with particle sizes of the catalyst, i.e. the granule particles, having a statistical distribution between 2.0 and 5.0 millimeters (mm), where up to 10 percent of the particles may also be outside said range of said lower limit or upper limit, but up to 10 percent in each case may also be outside said range of said lower limit and upper limit.

Preparation of IPDA with the Inventive Catalyst
The catalysts are tested for their catalytic efficacy in the preparation of 3-aminomethyl-3,5,5-trimethylcyclohexylamine (isophoronediamine, IPDA) from 3-cyano-3,5,5-trimethylcyclohexanone (isophoronenitrile, IPN) in a two-stage process.

In the first stage, isophoronenitrile is at least partly converted to 3-cyano-3,5,5-trimethylcyclohexane imine with ammonia in the presence of an imination catalyst and, in the second stage, subjected to aminating hydrogenation with hydrogen in the presence of ammonia over a hydrogenation catalyst at a temperature of 60-100° C. and a pressure of 250 bar. Each stage of the preparation is conducted in a separate reactor. However, the two reactors are connected in series and their temperatures are controlled individually.

The hydrogenation reactor is charged with 42 ml of the catalyst to be tested. The input solution of IPN (15% by weight) and ammonia (85% by weight) is pumped through the reaction tube from the top downward at a mass flow rate of 110 ml/h. The hydrogen is added separately, likewise from the top, at a volume flow rate of 40 l/h. The product liquid is collected in a collecting vessel beneath the reactor. The collected product mixture is analysed by gas chromatography for IPDA and corresponding secondary components. The results are listed in Table 1.

TABLE 1

| Temperature | IPDA yield/GC % | Conversion/% |
|---|---|---|
| 100° C. | 98.1 | 99.5 |
| 80° C. | 96.7 | 98.5 |
| 60° C. | 92.1 | 93.1 |

Long-Term Stability

In the first stage, isophoronenitrile is at least partly converted to 3-cyano-3,5,5-trimethylcyclohexane imine with ammonia in the presence of an imination catalyst and, in the second stage, subjected to aminating hydrogenation with hydrogen in the presence of ammonia over a hydrogenation catalyst at a temperature of 60° C. (inventive catalyst) or 100° C. (reference catalyst, supported compressed shaped cobalt body) and a pressure of 250 bar. Each stage of the preparation is conducted in a separate reactor. However, the two reactors are connected in series and their temperatures are controlled individually.

For the testing of long-term stability, the hydrogenation reactor is charged with 100 ml of the catalyst to be tested. The input solution of IPN (22% by weight) and ammonia (78% by weight) is pumped through the reaction tube from the top downward at a mass flow rate of 120 g/h. In addition, hydrogen is added, likewise from the top, at a volume flow rate of 50 l/h. The product liquid is collected in a collecting vessel beneath the reactor. The collected product mixture is analysed by gas chromatography for IPDA and corresponding secondary components. The results are shown in FIG. 1.

Inventive catalyst: cobalt granules of the composition as described above

Reference catalyst: supported compressed shaped cobalt catalyst bodies

The invention claimed is:

1. A process for preparing isophoronediamine, wherein
A) isophoronenitrile is subjected directly in one stage to aminating hydrogenation to give isophoronediamine in the presence of ammonia, hydrogen, a hydrogenation catalyst and possibly further additions, and in the presence or absence of organic solvents;
or
B) isophoronenitrile is first converted fully or partly in at least two or more than two stages to isophoronenitrile imine, and this isophoronenitrile imine is subjected to aminating hydrogenation to give isophoronediamine as a pure substance or in a mixture with other components and/or isophoronenitrile, in the presence of at least ammonia, hydrogen and a catalyst;
I. wherein the catalyst is a base surface activated metal alloy comprising, in its entirety, the following composition in percent by weight (% by weight), where the proportions add up to 100% by weight, based on the metals present:
cobalt: from 55% to 95% by weight
aluminum: from 5% to 45% by weight
chromium: from 0% to 3% by weight
nickel: from 0% to 7% by weight
and
II. the catalyst is in the form of granular material having particle sizes of from 1 to 8 millimeters (mm).

2. The process for preparing isophoronediamine according to claim 1, wherein
I.
the catalyst comprises:
cobalt: from 55% to 90% by weight
aluminum: from 5% to 44.5% by weight
chromium: from 0.5% to 5% by weight.

3. The process for preparing isophoronediamine according to claim 1, wherein
I.
the catalyst comprises:
cobalt: from 55% to 88% by weight
aluminum: from 5% to 44.5% by weight
nickel: from 0.5% to 7% by weight.

4. The process for preparing isophoronediamine according to claim 1, wherein
I.
the catalyst comprises:
cobalt: from 55% to 85% by weight
aluminum: from 5% to 43.5% by weight
chromium: from 0.5% to 3% by weight
nickel: from 1% to 7% by weight.

5. The process for preparing isophoronediamine according to claim 1, wherein
I.
the catalyst comprises:
cobalt: from 57% to 84% by weight
aluminum: from 10% to 40% by weight
chromium: from 1% to 2% by weight
nickel: from 2% to 4% by weight.

6. The process for preparing isophoronediamine according to claim 1, wherein
the particle sizes of the catalyst, vary from 2.5 to 6 millimeters (mm),
or
the particle sizes of the catalyst, vary from 3 to 7 millimeters (mm),
or
the particle sizes of the catalyst, vary from 2 to 5 millimeters (mm).

7. The process for preparing isophoronediamine according to claim 4, wherein the catalyst is obtained by screening the granules produced.

8. The process for preparing isophoronediamine according to claim 7, wherein the catalyst is obtained by screening the granules produced, and
the particle sizes of the catalyst, have a statistical distribution
between 2.5 and 5.5 millimeters (mm), or
the particle sizes of the catalyst, have a statistical distribution between 3.5 and 6.5 millimeters (mm), or
the particle sizes of the catalyst, have a statistical distribution between 2 and 5 millimeters (mm), or
the particle sizes of the catalyst, have a statistical distribution between 3 and 7 millimeters (mm),
and where up to 10 percent of the particles may also be outside said range of said lower limit or upper limit, but up to 10 percent in each case may also be outside said range of said lower limit and upper limit.

9. The process for preparing isophoronediamine according to claim 1, wherein the catalyst consists of, after the activation, in its entirety, the following composition in percent by weight (% by weight), where the proportions add up to 100% by weight, based on the metals present:
cobalt: from 57% to 84% by weight
aluminum: from 10% to 40% by weight
chromium: from 1% to 2% by weight
nickel: from 2% to 4% by weight
and with
particle sizes of the catalyst, having a statistical distribution between 2.5 and 5.5 millimeters (mm),
or
particle sizes of the catalyst, having a statistical distribution between 3.5 and 6.5 millimeters, (mm),
or
particle sizes of the catalyst, having a statistical distribution between 2 and 5 millimeters (mm),
or
particle sizes of the catalyst, having a statistical distribution between 3 and 7 millimeters (mm),
where up to 10 percent of the particles may also be outside said range of said lower limit or upper limit, but up to 10 percent in each case may also be outside said range of said lower limit and upper limit.

10. The process for preparing isophoronediamine according to claim 1, wherein the catalysts additionally comprise doping metals.

11. The process for preparing isophoronediamine according to claim 1, wherein the catalysts comprise modifiers, alkali metals and alkaline earth metals or compounds thereof, magnesium and lithium compounds.

12. The process for preparing isophoronediamine according to claim 1, wherein at least some of the isophoronenitrile imine used is converted in the first stage by reaction with ammonia in the presence or absence of an imination catalyst and/or of solvents to isophoronenitrile imine, the conversion of IPN to IPNI after the imination being greater than 80%.

13. The process for preparing isophoronediamine according to claim 1, wherein the first stage reaction product, as obtained or after a further treatment and/or addition of further ammonia, is subjected in the second stage to aminating hydrogenation over hydrogenation catalysts in the presence of at least ammonia and hydrogen and in the presence or absence of an organic solvent at a temperature of from 20 to 150° C., and a pressure of from 0.3 to 50 MPa.

14. The process for preparing isophoronediamine according to claim 1, wherein the conversion of IPN to IPDA is effected in three separate reaction spaces, IPN being converted to isophoronenitrile imine with excess ammonia over imination catalysts in the first reaction space at temperatures between 20 and 150° C. and pressures between 5 and 30 MPa, the reaction products formed being hydrogenated with hydrogen in the presence of excess ammonia over hydrogenation catalysts in the second reaction space at temperatures between 20 and 130° C. and pressures of from 5 to 30 MPa, and the reaction products formed being hydrogenated over catalysts in the third reaction space at temperatures between 100 and 160° C. and pressures of from 5 to 30 MPa.

15. The process for preparing isophoronediamine according to claim 1, wherein the imination reaction is effected in the presence of at least one imination catalyst.

16. The process for preparing isophoronediamine according to claim 1, wherein the imination of isophoronenitrile with liquid ammonia is conducted without addition of further solvent.

17. The process for preparing isophoronediamine according to claim 1, wherein between 1 and 500 mol, of ammonia is used per mole of IPN used in the imination stage.

18. The process for preparing isophoronediamine according to claim 1, wherein
the imination is conducted in the presence of a suspension catalyst, of at least one fixed bed catalyst.

19. The process for preparing isophoronediamine according to claim 1, wherein IPN and ammonia in the imination are conducted continuously from the bottom upward through a reaction tube filled with imination catalyst.

20. The process for preparing isophoronediamine according to claim 1, wherein the hydrogen required for the hydrogenation is supplied to the reactor either in excess, or in such an amount that the hydrogen consumed by reaction and the portion of the hydrogen which leaves the reactor dissolved in the product stream is replenished.

21. The process for preparing isophoronediamine according to claim 1, wherein the hydrogenation is conducted in liquid ammonia as solvent, using between 1 and 500 mol, of ammonia per mole of IPN.

22. The process for preparing isophoronediamine according to claim 1, wherein the hydrogenation catalysts are first conditioned with ammonia before they are used in the hydrogenation.

23. The process for preparing isophoronediamine according to claim 1, wherein the hydrogenation is effected continuously in fixed bed reactors.

24. The process for preparing isophoronediamine according to claim 1, wherein the hydrogenation is conducted continuously in fixed bed reactors which are operated in trickle mode or liquid phase mode.

25. The process for preparing isophoronediamine according to claim 1, wherein the reaction mixture leaving the hydrogenation is purified in one or more stages, and the isophoronediamine is obtained.

26. The process for preparing isophoronediamine according to claim 1, wherein the reaction mixture leaving the hydrogenation is purified in two steps, with complete or partial removal particularly of hydrogen, inert gases, ammonia, low-boiling impurities and optionally water in one or more distillation columns in a first step, and complete or partial removal of further low-boiling impurities, water and high-boiling impurities in distillation columns in a second step, and the isophoronediamine is obtained.

27. A catalyst for preparation of isophoronediamine, where the catalyst comprises the following properties:
I.
the catalyst consisting of, after the activation, the following composition in percent by weight (% by weight), where the proportions add up to 100% by weight, based on the metals present:
cobalt: from 55% to 95% by weight
aluminum: from 5% to 45% by weight
chromium: from 0.5% to 3% by weight
nickel: from 0.5% to 7% by weight
and
II.
the catalyst is in the form of granular material and, after the activation the catalyst is in the form of individual particles having particle sizes of from 1 to 8 millimeters (mm).

* * * * *